United States Patent [19]
Mauze et al.

[11] Patent Number: 6,038,922
[45] Date of Patent: Mar. 21, 2000

[54] THERMOMETRIC APPARATUS AND METHOD FOR DETERMINING THE CONCENTRATION OF A VAPOR IN A GAS STREAM

[75] Inventors: Ganapati R. Mauze, Sunnyvale; Vladimir Serikov, Richmond, both of Calif.

[73] Assignee: Agilent Technologies, Inc., Palo Alto, Calif.

[21] Appl. No.: 08/878,566

[22] Filed: Jun. 19, 1997

[51] Int. Cl.⁷ .................................................. G01N 25/64
[52] U.S. Cl. .......................................................... 73/335.08
[58] Field of Search .............................. 73/25.04, 29.01, 73/29.02, 335.06, 335.08, 77

[56] References Cited

U.S. PATENT DOCUMENTS

| | | | |
|---|---|---|---|
| 1,484,129 | 2/1924 | Hermann et al. | 73/335.08 |
| 1,586,351 | 5/1926 | Bristol et al. | 73/335.08 |
| 2,494,769 | 1/1950 | Mabey | 73/335.08 |
| 3,603,135 | 9/1971 | Kawaguchi | 73/29.02 |
| 5,048,336 | 9/1991 | Sugihara et al. . | |
| 5,460,041 | 10/1995 | Andes et al. | 73/335.08 |
| 5,608,374 | 3/1997 | Ikejiri . | |

OTHER PUBLICATIONS

"Humidity Sensor Theory and Behaivor", (1996), HyCal Tech Info, pp. 1–2.

Grate et al., "Surface Acoustic Wave Vapor Sensors Based on Resonator Devices", (1991), vol. 63(17), pp. 1719–1727, Anal. Chem.

Eisner et al., "Design and Development of a Micro–Thermocouple Sensor for Determining Temperature and Relative Humidity Patterns Within an Airstream", (1989), vol. 111, pp. 283–287, Journal of Biomechanical Engineering.

Tsuchitani et al., "A Humidity Sensor Using Ionic Copolymer and its Application to a Humidity–Temperature Sensor Module", (1988), pp. 375–385, vol. 15, Sensors and Actuators.

"IC Humidity/Temperature Sensor", (1993), (3 pgs.), HY–CAL Engineering (A Unit of General Signal).

MiniCap 2, "Relative Humidity Sensor", (3 pgs.)

W.L. McCabe et al., "Huidification operations", Unit Operations of Chemical Engineeringf, 2nd ed., Chap. 22, pp. 678–706, McGraw Hill, Inc.

R.H. Perry & Chilton (ed.), "Psychrometry", pp. 12–2 to 12–5, Chemical Engineers' Handbook, 5th ed., Section on Psychrometry by F. H. Fuller (Section 12) in portion.

*Primary Examiner*—Daniel S. Larkin

[57] ABSTRACT

A sensor for sensing the concentration of a vapor of a volatile liquid in a gas is disclosed. The sensor has a dry-transducer temperature sensor and a wet-transducer temperature sensor. The wet transducer-temperature sensor is covered by a non-woven, non-flaking, liquid-permeable material to allow the liquid to pass from a source to about the wet-transducer temperature sensor and vaporize when the gas is not saturated with the vapor. The vaporization of the volatile liquid causes the temperature at the wet-transducer temperature sensor to have a steady-state temperature lower than the reference temperature measured by the dry-transducer temperature sensor. The difference in the temperature measured by the two temperature sensors being determinable to determine the concentration of the vapor in the gas. In an embodiment, the non-woven, non-flaking, liquid-permeable material is a porous membrane. In another embodiment, it is a gel.

24 Claims, 5 Drawing Sheets

THERMOMETRIC APPARATUS AND METHOD FOR DETERMINING THE CONCENTRATION OF A VAPOR IN A GAS STREAM

FIELD OF THE INVENTION

The present invention is related to techniques for determining the concentration of a vapor in a gas stream and, more particularly, to apparatuses and methods for determining the humidity in an air stream as a result of wet-bulb and dry bulb temperature difference.

BACKGROUND

The measurement of the concentration of a vapor in a gas is often important For example, it is useful to know the concentration of flammable gases in a gas stream in combustion technology. The humidity of air in an area is of interest to people concerned about the weather. Further, in health care, an anesthesiologist would want to know the concentration of an anesthetic in a gas stream administered to a patient during surgery. The concentration of water vapor in the exhaled air of a person can indicate the functioning condition of the person's respiratory system. The detection of temperature and moisture content of air being inhaled and exhaled will provide valuable information to health care professionals on aerosol therapy and toxicology of toxic gases inhalation.

Vapor concentration sensors based on measuring the mass of vapor absorbed on polymer films coated on surface acoustic wave devices have been developed. For example, Jay W. Grate and Mark Kluxty, *Anal. Chem.*, vol. 63, pp 1719–1727 (1991), describe a humidity sensor in which vapor absorption changes the frequency of oscillation of mass-sensitive resonators. Also, Polymer-based impedance effect humidity sensors are disclosed by S. Tsuchitani et al. in "A humidity sensor using ionic copolymer and its application to a humidity—temperature sensor module," *Sensors and Actuators*, Vol. 15, No. 4, pp 375–386, 1988. In the Tsuchitani humidity sensors, moisture absorption by ionic copolymers causes a change in impedance in an electrical circuit, thereby causing a change in oscillation frequency. However, vapor concentration sensors by vapor absorption are not very specific and are subject to interference by any absorbable vapor that has not be present in a calibration sample. Moreover, such vapor sensors do not work well near the condensation point because they may not respond to a fall in humidity quickly. Therefore, a need exists for a highly specific vapor concentration sensor that will function over a wide range of concentrations.

Humidity sensors have been used for many years to determine air humidity for weather reporting. For such applications, one simple kind of humidity sensor has a dry bulb thermometer and a wet bulb thermometer. The wet bulb thermometer has a thermometer with a bulb moistened by a wick. Generally water passes by capillary action against gravity up the wick from a container. Water evaporates from the wick when the air is unsaturated with water vapor. Due to the cooling effect of the evaporation of water from the wick, the temperature of the wet thermometer will be lower than the true temperature of the air had there been no evaporation. The temperature of the wet thermometer is known as the "wet-bulb temperature." The temperature that is measured by a dry thermometer, known as the "dry-bulb temperature," and the wet-bulb temperature are used to determine the humidity in air. See, for example, McCabe and Smith, *Unit Operations of Chemical Engineering*, McGraw-Hill, Ch. 24, 3rd ed., (1956). Such humidity sensors tend to be large and requires a generally upright position to keep the liquid water in place. Their response time is typically not very fast.

More recently, moisture sensors employing microthermocouple sensors for determining temperature and relative humidity in an airstream have been reported, for example, in "Design and development of a microthermocouple sensor for determining temperature and relative humidity patterns within an airstream," *J Biomechan. Eng.* Vol. 111, PP. 283–287, Nov. 1989. In such a device, a wet-bulb thermocouple junction is coated with a sprayed-on boron nitride coating, which is reported to be hard and porous. A sleeve is used to supply water to the boron nitride coating. It would appear that coating a thermocouple junction by spraying is not an easy task and one has to take special care to position the sleeve precisely to wet the boron nitride coating without leakage. It is also difficult to form a boron nitride coating that is stable on metal or glass surfaces. Moreover, to get a porous structure suitable for conducting water adequately one needs to form a boron nitride layer that is quite thick, making it brittle and slow to transfer heat.

Therefore, a need exists for a dry-bulb-wet-bulb vapor concentration sensor that is relatively simple to construct, and particularly for a dry-bulb-wet-bulb vapor concentration sensor that is sturdy.

SUMMARY

In one aspect, the present invention provides a sensor for sensing the concentration of a vapor of a vaporizable liquid in a gas stream. An embodiment of the sensor includes a wetable temperature sensor having a heat sensitive part and a liquid-permeable member (LPM) surrounding the heat sensitive part. The LPM provides a surface for evaporation of the liquid into the measuring gas stream such that the temperature sensitive part achieves fast temperature equilibrium with the neighborhood of the evaporating surface. To determine the concentration of a vapor of a liquid in the gas stream, the LPM filled with the liquid is placed in the gas stream. Heat loss due to evaporation of the liquid in the gas stream from the LPM will result in the temperature sensed by the wetable temperature sensor being lower than the temperature of the gas stream, as determined by a dry temperature sensor. This difference between the two temperatures can be determined to obtain the concentration of the vapor in the gas stream. Preferably, the LPM is made of a liquid-permeable, non-woven, non-flaking material.

With the present invention, a fast vapor concentration sensor can be made, even for applications that require small dimensions and independence to the position relative to the gravitational field. The sensor of the present invention is advantageous over conventional sensors with woven wicks. First, regarding woven wicks, it is difficult to form a woven material that can wrap uniformly around a temperature sensitive unit such as a thermistor head or thermocouple junction to provide adequate liquid without dripping. Also, there may be a tendency for fibrous material to become unwoven and come off, which is not desirable in certain applications, such as in an airway of a patient. Similarly, materials that are brittle and fragile, such a boron nitride, may flake off, leading to undesirable patterns of heat and mass transfer as well. In conventional wick-type humidity sensors, water is drawn against gravity by capillary action through a fibrous wick from water in a container to a thermometer. This is not conducive for using the humidity sensor in hard-to-reach places since the water container and the wick render the wet-bulb thermometer hard to position. A wickless embodiment of a vapor concentration sensor according to the present invention can be used in hard-to-reach places such as the airway of a patient. As used herein, the term "wickless" means the lack of a material that conducts liquid by capillary action against gravity from a liquid container.

Sensors can be made according to the present invention to be highly specific to the vapor for which the concentration information is desired. For example, an alcohol vapor concentration sensor can be made by wetting the LPM with alcohol. Such a vapor concentration sensor will operate well to measure the concentration of alcohol in a gas stream despite the presence of other vapors in the gas stream. The driving force for the evaporation of alcohol at the wet junction is independent of the vapor pressure of other volatiles in the gas stream. Such specific sensors are advantageous over absorption vapor concentration sensors because the rate of vapor absorption of such absorption vapor concentration sensors is affected by the presence of other vapors in the gas. Another advantage of the sensor of the present invention is that by merely changing the liquid, the same apparatus hardware can be used for measuring the concentration of different vapors chemically compatible with the apparatus hardware.

In an embodiment according to the present invention, a gel is used as the LPM to surround the wetable temperature sensor and to conduct a liquid from a supply of the liquid to the wetable temperature sensor. Such a gel can be covalently bound to the wetable temperature sensor to further provide mechanical integrity. In another embodiment, a porous material is used as the LPM to confine a liquid to surround the wetable temperature sensor and to conduct the liquid from a supply of the liquid to the wetable temperature sensor. In both embodiments, the structures can be made robust to tolerate rough handling. They can also be made with biocompatible materials that are sterilizeable with steam, ethylene oxide, gamma radiation, and the like.

BRIEF DESCRIPTION OF THE DRAWINGS

The following figures are included to better illustrate the embodiments of the apparatus and technique of the present invention. In these figures, like numerals represent like features in the several views.

DETAILED DESCRIPTION OF THE INVENTION

In one aspect, the present invention provides a technique for vaporing a liquid from a non-woven surface such that the decrease in temperature due to the latent heat of evaporation can be measured to determine the concentration of a vapor of the liquid in a gas.

Figure 1:
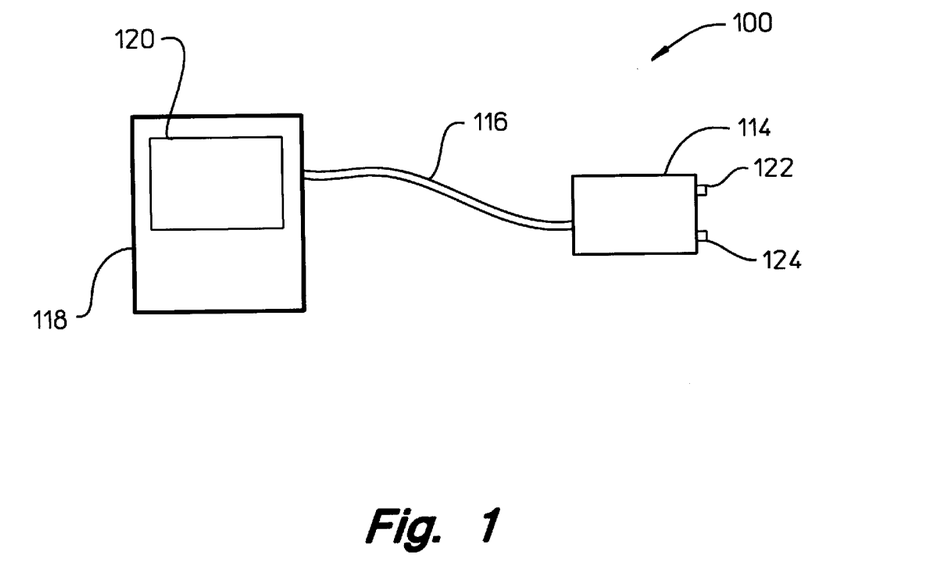
FIG. 1 shows an embodiment of a vapor concentration sensor according to the present invention.

FIG. 1 shows an embodiment of a vapor concentration sensor of the present invention for measuring the concentration of the vapor of a volatile liquid in a gas. The vapor concentration sensor (or apparatus) 100 has a "dual-transducer temperature sensor" 114 connected by means of an electrical cable 116 to a processor 118 for processing the temperature data from the dual-transducer temperature sensor 114 to indicate the vapor concentration in the gas. The humidity (or concentration of the vapor) can be displayed in a display device 120 such as a computer monitor, liquid crystal display, light emitting diode display, paper printer, plotter, galvanometer with a indicator needle, and the like. The dual-transducer temperature sensor 114 has a reference temperature sensor 122 for measuring the temperature of the gas and a wet-transducer temperature sensor 124 for measuring the temperature of a wet material, which will lose the liquid to the gas by vaporization at a rate dependent on the degree of unsaturation of the vapor of the liquid in the gas. As used herein, the term "wet-transducer temperature sensor" refers to a temperature sensing device, whether electronic or mechanical, that is used to measure the temperature of the material surrounding the temperature sensor wherein the material loses liquid by evaporation to the gas surrounding the material. As a result, the material cools to a steady state temperature lower than that of the gas due to the latent heat of evaporation. The wet-transducer temperature sensor is "wetable" in the sense that the liquid can wet this sensor to enable the apparatus to sense the vapor concentration.

Figure 2:
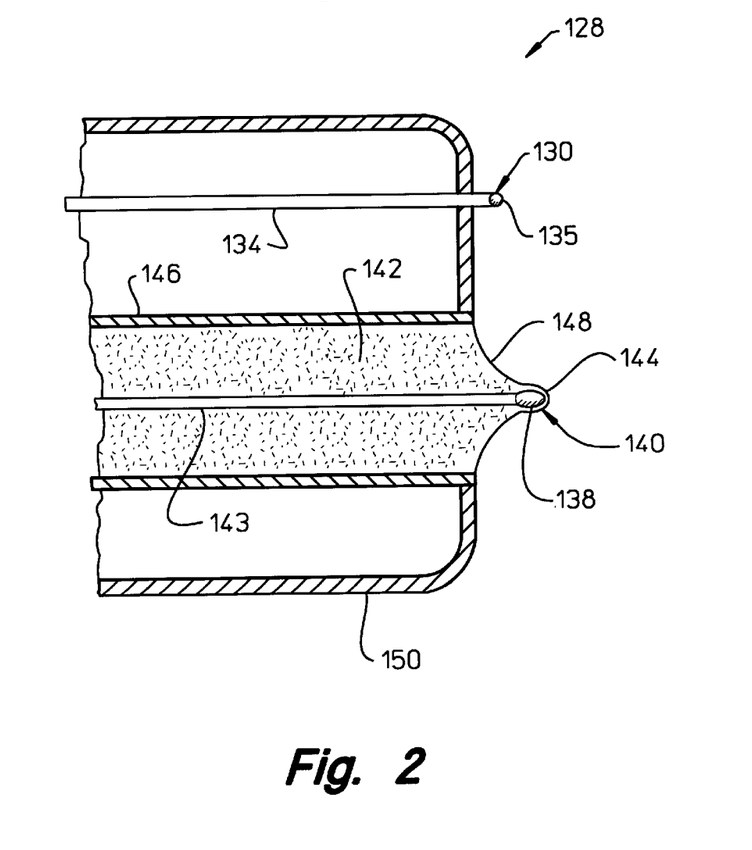
FIG. 2 shows an embodiment of a dual-transducer temperature sensor that can be used for the vapor concentration sensor of FIG. 1.

FIG. 2 shows an embodiment of a dual-transducer temperature sensor that can be used for the vapor concentration sensor of FIG. 1. In this embodiment, the dual-transducer temperature sensor 128 has a thermocouple 130 for measuring the reference temperature of the gas. In this embodiment, the thermocouple 130 is not wetted by a liquid, thus its temperature is referred to as the "dry-transducer temperature." Wires (not shown in FIG. 2) connected to the thermocouple 130 are enclosed in a cable 134 for transmitting electrical signals representing temperature distally to the processor 118. As used herein, "proximal" refers to a direction that is away from the tip, which contains the temperature sensitive part, of the temperature sensor (e.g. thermocouple 130, which has a tip 135). "Distal" refers to a direction remote from the proximal direction, i.e., towards the tip of the temperature sensor.

In the neighborhood, or vicinity, of the reference thermocouple 130 is a "wet-transducer" temperature sensor, in this case a thermocouple 138, which has a gel coating 140 thereon. The gel coating, which encloses the temperature sensitive head 144 of the wet-transducer thermocouple 138, is considered to "substantially surround" the thermocouple. The gel in the gel coating 140, in this embodiment for detecting water humidity in air, is a hydrogel in which water can permeate from a body of gel 142 proximal to the temperature sensitive head 144. The volume of the body of gel 142 is significantly larger than that of the gel coating 140 such that as water evaporates from the gel coating 140 about the thermocouple temperature sensitive head 144 water can migrate from the body of gel 142 to the gel coating 140. The migration of water is preferably adequate to maintain the water concentration in the gel coating 140 substantially constant for a period adequately long for the temperature of the wet-transducer thermocouple 138 to come to a steady state temperature after the dual-transducer temperature sensor 128 is put into an air stream to measure its humidity. The wires connected to the wet-transducer thermocouple 138 pass through the body of gel 142 via a cable 143. It is preferred that water does not drip from the wet-transducer temperature sensor 138 because such water drips will carry away thermal energy, change the heat and mass transfer surface, and affect the thermal energy balance between the latent heat of evaporation and the decrease of temperature of the gel coating 140 and the wet-transducer temperature sensor 138.

A water-impermeable shell 146 encircles the body of gel 142 to prevent water evaporation from the body of the gel 142. The distal portion of the body of gel 142 is not covered by the shell such that a transition zone 148 gradually reduces the thickness of the gel to that of a thin gel coating 140 surrounding the temperature sensitive head (i.e., the thermocouple junction or equivalent thereof, e.g., the thermistor head of a thermistor) 144 of the wet-transducer thermocouple 138. The transition zone 148 and the gel coating 140 provide adequate gel volume to maintain a layer of wet gel around the wet-transducer thermocouple head 144 such that preferably, the layer of gel is not water-mass-transfer-limited. Preferably, as water evaporates from the gel coating 140, an adequate amount of water can permeate from the body of gel 142 to allow the wet-transducer thermocouple head 144 to come to a steady state temperature once placed in a desired location. Under normal operating conditions of the vapor concentration sensor 100, for example, between about 1° C. and 45° C. for relative water humidity of about 1% to 100% saturation, being not water-mass-transfer-limited, the gel-coating will have a higher rate of evaporation at a lower relative humidity than at a higher relative humidity at the same temperature. The reference thermocouple 130 and the wet-transducer thermocouple 138 are held in close proximity to each other by a support body 150 such that they sense temperature of air portions that are close enough to have essentially the same temperature and humidity. It is preferred that the gel coating be uniformly hydrated around the thermocouple junction and that no dry spot is present so that the heat transfer coefficient stays relatively constant for a steady state to establish. To make the dual-transducer temperature sensor, a well wetted gel can be put into the shell. Before using the dual-transducer temperature sensor, the distal end of the wet-transducer temperature sensor can be put into a suitable liquid to wet the gel. After the gel is well wetted, the exposed part of the gel can be wrapped in a suitable material to prevent the liquid from evaporating until placed in the gas stream the humidity of which is to be measured.

Examples of preferred gels for use in making the wet-transducer temperature sensor are made from polymeric materials, including poly(hydroxyethyl methacrylate), polyacrylamide, poly(vinyl alcohol), and poly(ethylene glycol), and the like. The thickness of the gel coating in the presence of liquid can be about 20 $\mu$m to 1,000 $\mu$m, preferably 30 $\mu$m to 200 $\mu$m, more preferably about 40 $\mu$m to 100 $\mu$m, even more preferably about 50 $\mu$m. Depending on the application (e.g., whether the liquid is alcohol or chloroform, or whether the sensor is to be used in the airway of a man or in a pipe with 4-inch inside diameter), the thickness of the gel coating on the thermocouple head can be made to suit the specific application. For example, if the application is a humidity sensor for measuring the water humidity in the airway, e.g., the trachea, of a mammal such as a human, the dual-transducer temperature sensor should be small enough to fit into the airway and respond fast enough to the air flow during a relatively steady exhaling phase of the mammal. In this case, the preferred thickness of the gel coating is about 40 $\mu$m to 80 $\mu$m, more preferably about 50 $\mu$m for a dual-transducer temperature sensor to be used in human. For a large pipe with a steady gas flow, a slower heat and mass transfer rate can be tolerated and a thicker gel layer can be used. For a liquid that wets the gel material well, the liquid can permeate through the gel quickly and a thicker gel layer can be tolerated than otherwise.

The gel, which is a medium through which the liquid permeates, extends from the gel coating around the thermocouple heat sensitive head proximally to the liquid supply, which is the body of gel. Preferably the gel is substantially homogenous to conduct the liquid evenly. Such continuous gel coatings on the wet-transducer temperature sensors can provide good liquid transfer without liquid leakage, as can happen with water supplied from a sleeve positioned near to a hard, sprayed-on boron nitride coating on a thermocouple if the sleeve is too far back from the thermocouple junction.

For water humidity sensors, the water content of the fully hydrated hydrogel is preferably about 5% to 20% by weight, more preferably about 10% by weight of the hydrated gel. The temperature sensor and the water content and permeability of the gel can be controlled during the formation of the gel to provide adequate liquid flow rate and response time of the vapor concentration sensor. To prevent the gel from breaking off, the gel can be covalently bound to the temperature sensor, which can have a metallic, glass, or polymeric surface. Techniques for preparing and using gels, as well as for covalently binding polymeric gels, are known in the art. For example, see, Tsutsumi et al., *J Polym. Sci.*, Part A, Polymer Chemistry, V. 31, No. 12, P 2883 (1993), the description of which regarding the preparation and use of gels are incorporated by reference herein. It is to be understood that although a gel for determining water humidity is described, a person skilled in the art can form a gel-containing vapor concentration sensor based on the present disclosure for other vapors, including polar or water miscible material, e.g., alcohols, and the like, without undue experimentation.

Figure 3:
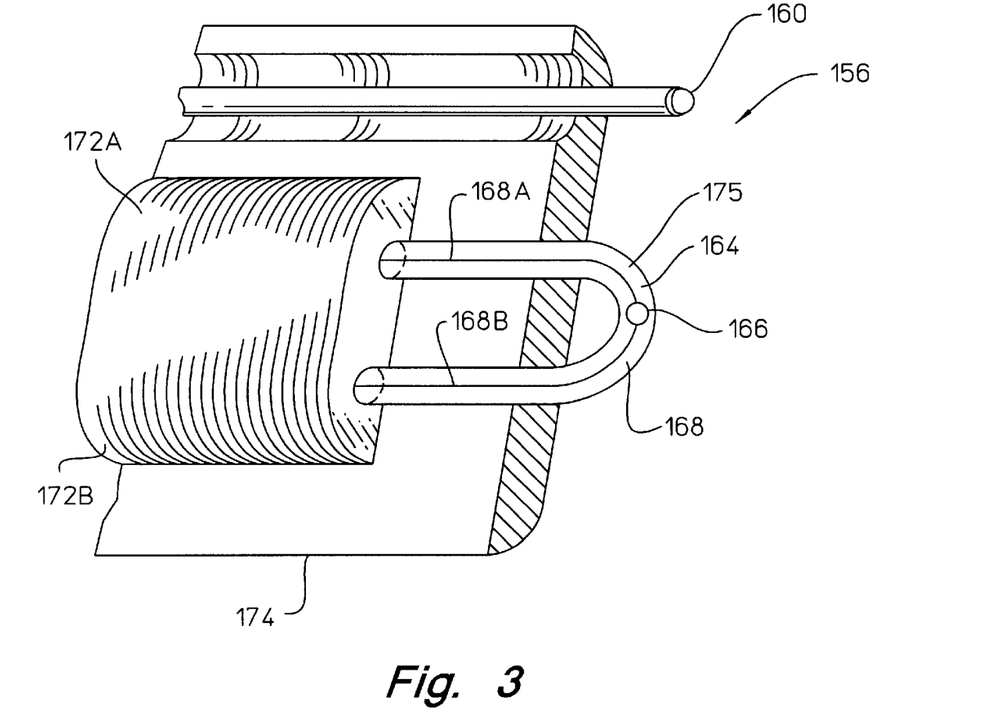
FIG. 3 shows a partially cut-out perspective view in portion of a dual-transducer temperature sensor in accordance with the present invention
Figure 4:
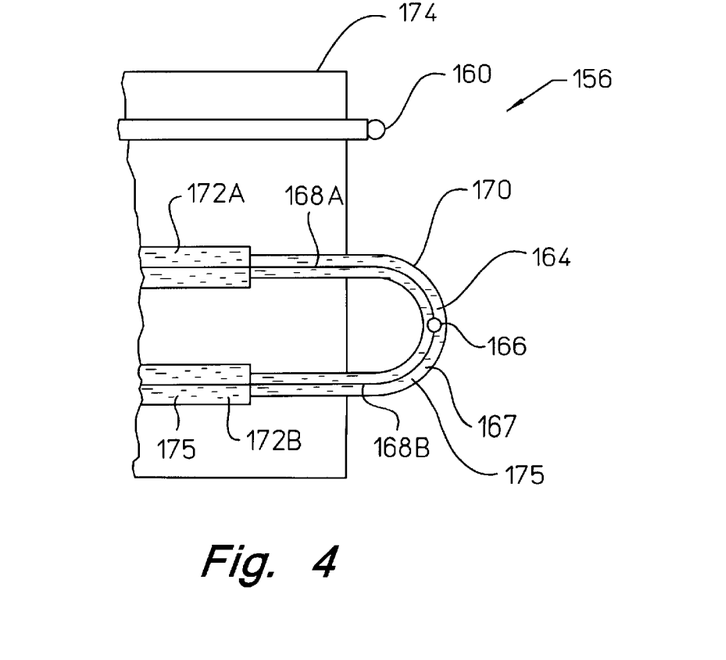
FIG. 4 shows a plan view in portion of the dual-transducer temperature sensor of FIG. 3.

Another embodiment of the sensor for determining vapor concentration in a gas is shown in FIGS. 3 and 4. FIG. 3 shows a partially cut-out perspective view of the sensor, for example, a water-humidity sensor. FIG. 4 shows a plan view of the same. The water-humidity sensor has a dual-transducer temperature sensor 156, which has a reference temperature sensor 160. The reference temperature sensor 160 in turn can be a thermocouple similar to the reference thermocouple of FIG. 2. Near to the reference temperature sensor 160 is the wet-transducer temperature sensor 164, in this example a thermocouple having a temperature sensitive thermocouple head (or junction) 166. The thermocouple is contained in a cavity 167 that contains liquid water. In this embodiment a U-shaped tubing 170 of a water-porous membrane substantially defines the cavity 167 and contains liquid water 175 and the wet-transducer temperature sensor 164. The U-shaped tubing is joined at its two ends to a water-containing reservoir 172A and a water-containing reservoir 172B, which supply water 175 to flow to surround the wet-transducer temperature sensor thermocouple head 166 as water permeates the membrane of the tubing 170 to be evaporated. The tubing 170 is considered to "substantially surround" the thermocouple. It is contemplated that the reservoirs 172A and 172B can be joined as a single chamber or be separate. The reservoirs 172A and 172B can also be separate such that water 175 is flowed from one reservoir via the U-shaped tubing 170 to the other reservoir. In this way, the humidity sensor can be pointed in any direction and the thermocouple head 166 will still be immersed without any void between the thermocouple head 166 and the membrane of U-shaped tubing 170, thereby providing efficient heat and mass transfer. The water 175 in the tubing 170 can be considered to be the medium through which water is transferred to about the thermocouple heat sensitive junction (i.e., thermocouple head 166). If desired, a pump (such as a positive displacement pump) can be used to slowly push the liquid to about the thermocouple head 166 as the liquid evaporates. Also, one or both of the reservoirs can be a closed (except where they connect to the tubing 170), adjustable-volume container, e.g., with a flexible wall, such that as the liquid evaporates, the volume of the reservoir(s) can shrink to provide the liquid to about the thermocouple head 166.

Preferably water does not flow past the thermocouple head 166 at a fluctuating rate or at a rate that would significantly affect the energy balance between the heat loss by evaporation and the heat transferred due to the temperature difference between gas and the water. The membrane is advantageous over a sprayed-on boron nitride coating in that the sprayed on coating is more fragile than the tubing and may flake or chip. When the wet-transducer temperature sensor is used in a gas flow channel, any flake or chip formed may fall into the channel. Such flakes and chips are undesirable, particularly when the channel is the airway of a person. The boron nitride coating, which tends to be thick, also insulates the wet-transducer temperature sensor, leading to slow response. Boron nitride coating cannot be used easily for many vapors since the viscosity and chemical reactivity of many volatile liquids are incompatible with boron nitride coating or cause the liquids to drip. In the embodiment shown in FIGS. 3 and 4, the medium, e.g., water, is continuous from the thermocouple head to the proximal liquid (e.g., water) supply, i.e., reservoirs 172A and 172B.

The thermocouple head 166 is connected to wires 168A and 168B for communicating electrical signals representing the temperature data from the thermocouple head 166 to the processor 118. The reference temperature sensor 160 and the wet-transducer temperature sensor 164 are held together in proximity by a thermally insulating support body 174, which, for example, can be made of a polymeric material such as silicone, epoxy, rubber, polytetrafluoroethylene, and the like. It is preferred that the membrane of the U-shaped tubing 170 is not water-mass-transfer-limited such that water can migrate through the membrane at a rate responsive to a change of the degree of water-vapor unsaturation and temperature of the gas surround the dual-transducer temperature sensor 180.

Figure 5:
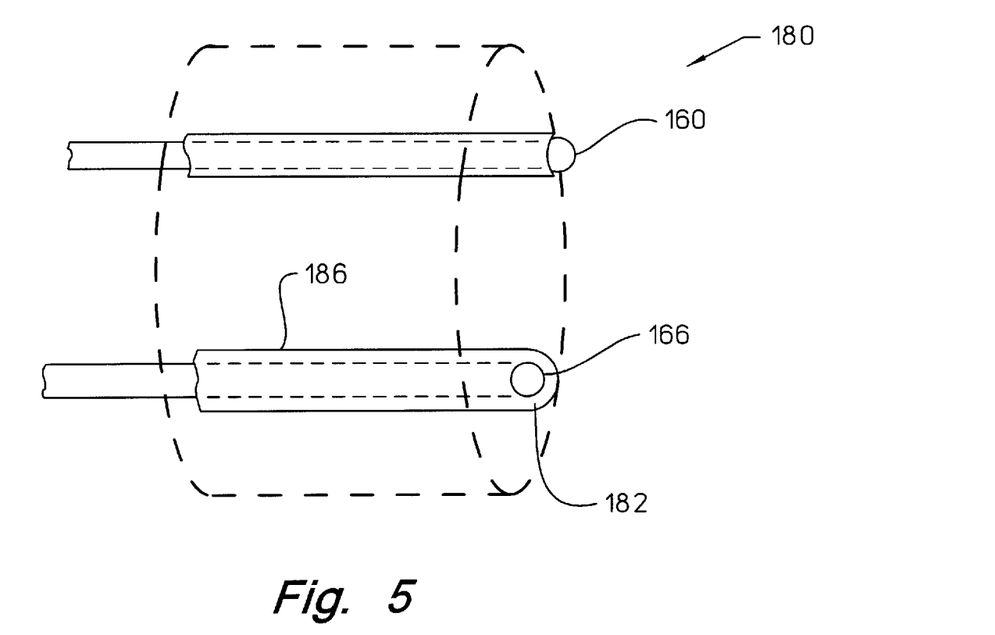
FIG. 5 shows a plan view in portion of yet another dual-transducer temperature sensor in accordance with the present invention.

In another embodiment of the vapor concentration sensor of the present invention, shown in FIG. 5, the dual-transducer temperature sensor 180 has a reference temperature sensor 160 and a wet-transducer temperature sensor 182. In this embodiment, the wet-transducer temperature sensor 182 has a thermocouple head 166 surrounded by a water-porous tubing 186, which is filled with water. The wet-transducer temperature sensor 182 will be operational if there is no void area between the thermocouple head 166 and the water-porous tubing 186.

The porous membrane for the cavity surrounding the wet-transducer temperature sensor can be made from a variety of polymeric materials. For example, for water humidity measurement, tubings of porous polymeric membranes such as porous membranes of polyolefin, polysulfone, cellulose, and derivatives thereof can be used. Preferred porous polyolefin membranous tubings include porous polypropylene tubing, expanded polyethylene tubing, and cellulose tubing. The more preferred are hydrophilic membranous tubing such as cellulose, poly(vinyl alcohol), poly(vinyl ether), their derivatives, and the like. In such membranes, a pore size larger than the molecular weight (MW) of the volatile liquid can be used for volatile liquid permeation (e.g., water transport through the pores). However, the pore size is preferable not too large that dripping occurs. For example, the membrane can have a nominal molecular weight cutoff that falls between about 20 and 20,000 Daltons. Preferably, the upper range of the nominal molecular weight cutoff falls between about 100 and 1,000 Daltons to prevent dripping. Preferably, the membrane surrounding the wet-transducer temperature sensor is not a homogenous polymeric material such as a silicone membranous tubing. Rather, it is preferred that the porous membrane has pores for liquid to pass through so as to allow faster mass-transfer through the membrane. An example of a hydrophilic porous membrane suitable for use for a water-humidity sensor is CUPROPHAN V0.021 cellulose tubing (by Enka Glanzstoff AG, Charlotte, N.C., now a subdivision of AKZO Nobel Frazer AG, 28 Oehder Strasse, 42201, Wuppertal, Germany) of about 2.5 mm length and about 0.007 inch (175 $\mu$m) inside diameter (i.d.) and 0.01 inch (250 $\mu$m) outside diameter (o.d.). As an alternative, porous tubing of similar dimensions made of hydrophilic polypropylene can be obtained from Biogeneral Fiber Technology, 9925 Mesa Rim Road, San Diego, Calif. 92121. Such membranous tubing can be used for an alcohol vapor concentration sensor as well.

The selection of the polymeric porous membrane is done with consideration of the physical and chemical properties of the volatile liquid such that the membrane is chemically stable in the liquid and the viscosity and volatility is suitable for the temperature difference measurement in the range interested. For example, polytetrafluoroethylene may be better suited for chloroform than silicone rubber since silicone rubber may degrade in chloroform. Polysulfone membranes are resistant to chemical attack by many volatile liquids. Chemical compatibility of membranes, viscosity and volatility data for many common liquids, e.g., methanol, ethanol, acetone, chloroform, dimethyl ether, and benzene are known in the art or can be determined by routine experimentation. Because a polymeric membrane can be suitable for more than one volatile liquid, sometimes the same apparatus can be used for determining the vapor concentration of different volatile liquids by changing the liquid in the apparatus. For example, the same porous cellulose membranous tubings can be used for determining the vapor concentration of water and for methanol. Polysulfone membranous tubings can be used for determining the vapor concentration of some alcohols, chloroform, and acetone.

As with the dual-transducer temperature sensor having a gel coating shown in FIG. 2 and described above, the choice of the size, dimensions, and membrane characteristics of the dual-transducer temperature sensor with a porous membrane is dependent on the application. For faster responses, the diameter of the porous membranous tubing is preferably just large enough to surround the wet-transducer temperature sensor, e.g., the thermocouple head (i.e., the thermocouple junction). Such a tubing size reduces the amount of material the temperature of which needs to be decreased by heat loss due to evaporation. As a result, heat transfer from the tubing outside surface to the thermocouple will be more efficient The tubing is large enough to allow water to access the thermocouple head. For example, in an embodiment having a thermocouple head of about 150 μm in diameter, a porous tubing of about 200 μm nominal inside diameter can be used. A dual-transducer temperature sensor having a wet-transducer temperature sensor of this size will be applicable in measuring the water-humidity of air in a patient's airway.

It is to be understood that the porous membrane need not be a tubing to work according to the present invention. For example, a channel can be made with a non-membranous material and covered on one side with the porous membrane. This would be practicable if the wet-transducer temperature sensor is placed in the channel close to the membrane to allow fast heat and mass transfer.

A vapor concentration sensor of the present invention can be used in a gas stream to measure the vapor concentration of a liquid in the gas stream relatively independent of the velocity of the gas stream. Although water-humidity examples are described in more detail in this disclosure, it is to be understood that a vapor concentration sensor according to the present invention can be made to sense the concentration of the vapor of other liquids, such as organic liquids including alcohols, e.g., ethanol, methanol, propanol, isopropanol, butanol; ketone, e.g., acetone; aldehyde, e.g., formaldehyde; aromatic liquid, e.g., benzene and toluene; chlorinated organic such as carbon tetrachloride, and the like. As used herein, the term "humidity" refers to the degree of saturation of a vapor of a liquid in a gas, wherein the vapor may be water vapor or a vapor of other liquids and the gas may be air or other gases. In a more specific sense, as in equations herein, humidity refers to the concentration of the vapor in the gas expressed as mass of the vapor in unit mass of a vapor-free gas.

To use a humidity sensor of the present invention, a look up table, graph, or computer database can be obtained by calibrating a humidity sensor with a specific kind of dual-transducer temperature sensor with conditions corresponding to various concentrations and temperatures in a specific gas. For example, a psychrometric chart or graph for water vapor in air can be obtained by calibrating a humidity sensor with different samples of air having a variety of water vapor concentration in air at different temperature. Furthermore, such data can be stored electronically in a digital computer such that the electrical signals generated by the reference temperature sensors and the wet-transducer temperature sensors can be correlated with the vapor concentration in the gas sample and temperature. The computer can be programmed to indicate the corresponding vapor concentration depending on the electrical signals of the reference and wet-transducer temperature sensors. As used herein, the terms "psychrometry" and "psychrometric" refers to the determination of the concentration of a vapor of a vaporizable (i.e., volatile) liquid in a gas. Examples of vaporizable (volatile) liquids are those that have a vapor pressure at room temperature of 0.1 mmHg or above.

Other than a thermocouple, it is to be understood that other temperature measuring devices (i.e., temperature sensors), such as thermistors, and mechanical thermometers, e.g, liquid thermometers such as alcohol thermometers, mercury thermometers, unequal coefficients of expansion thermometers, and the like, can be used. In the case wherein the temperature sensors do not produce electrical signals, the temperature data can be read, e.g., by a person, and the humidity be determined by comparing with data in a graph, chart, or table.

The theory of psychrometry is known in the art. For example, publications such as McCabe and Smith, *Unit Operations of Chemical Engineering*, McGraw-Hill, Ch. 24, 3rd ed, (1956) and Robert Perry (ed.), *Chemical Engineers' Handbook*, Chapters on "Psychrometry" and "Solids drying fundamentals," McGraw-Hill (1963) describe humidification operations, psychrometric charts, and the theory of wet-bulb temperature versus dry-bulb temperature. Briefly, the dry-transducer temperature, corresponding to the dry-bulb temperature of McCabe or Perry, as measured by the reference temperature sensor in the present invention, represents the temperature of the gas in which the vapor content is to be determined. The wet-transducer temperature, corresponding to the wet-bulb temperature of McCabe or Perry, is the steady state, non-equilibrium temperature reached by a small mass of liquid under adiabatic conditions in a continuous stream of gas. In the present invention, as long as the liquid does not move past the wet-transducer temperature sensor in an excessive rate, the conditions approximates an adiabatic condition to the humidity sensor to be functional.

When the dual-transducer temperature sensor is placed in a gas stream, initially the temperature of the wet-transducer temperature sensor is about equal to or would tend to approach that of the gas, much like what the reference temperature sensor would do. If the gas is not saturated with the vapor of the liquid in question, liquid would evaporate from the liquid surrounding the wet-transducer temperature sensor. Because the condition is adiabatic, the latent heat of vaporization is supplied from the wet-transducer temperature sensor and the liquid, as well as the gel or the porous tubing surrounding them. As the temperature of the wet-transducer temperature sensor falls below that of the gas, sensible heat is transferred from the gas to the wet-transducer temperature sensor via the liquid surrounding it. Eventually a steady state is reached, at which point the heat supplied by the gas surrounding the wet-transducer temperature sensor to the liquid is equal to the heat loss by evaporation of the liquid in the vicinity of the wet-transducer temperature sensor and the wet-transducer temperature sensor settles at a temperature, the wet-transducer temperature. For the steady state to occur in a condition better suited for measuring humidity, it is more preferred that liquid be supplied to the wet-transducer temperature sensor at the wet-transducer temperature sensor and that the velocity of the gas passing over the wet-transducer temperature sensor be adequately large that radiation heat transfer is small compared to conduction and convention heat transfer between the gas and the liquid, and that the surface area from which water can evaporate stays constant. It is also preferred that liquid does not drip from the porous, membranous tubing so that the surface from which the liquid evaporates stay relatively constant and that the heat and mass transfer coefficients between the porous membrane and the gas stay relatively constant.

The heat transfer can be represent by the following equation:

$$q = M\,N\{L_w + C(t-t_w)\} \qquad \text{Eq. (1)}$$

where q is the rate of sensible heat transferred to the liquid, M is the molecular weight of the vapor evaporated from the liquid, N is the molal rate of transfer of vapor, $L_w$ is the latent heat of vaporization of the liquid, C is the heat capacity of the vapor, t is the temperature of the gas, and $t_w$ is the wet-transducer temperature. Because the value of the term "$C(t-t_w)$" is usually very small compared to $L_w$ in Eq.

(1), the relationship between humidity and the wet and dry-transducer temperature can be shown by the following equation:

$$(H-H_w)L_w = -K(t-t_w)$$ Eq. (2)

where H is the humidity in question, $H_w$ is the saturation humidity at the wet-transducer temperature $t_w$, $L_w$ is the latent heat of the vaporization of the liquid at temperature $t_w$, and K is s constant that depends on the molecular weight of the dry gas, the heat transfer coefficient, and the mass transfer coefficient between the liquid and the gas. Data for different conditions on the parameters in Eq. (2) can be obtained by routine experimentation by one skilled in the art. Such data for some common liquid and vapor mixtures are available in the literature. For example, psychrometric data in graphical form are available for air-water mixture, air-benzene, air-toluene, air-carbon tetrachloride in Perry, supra. Based on such data, after obtaining the reference temperature and wettransducer temperature, one can determine the humidity by looking up the data. Knowing the temperature of the gas stream, relative humidity (in %) and absolute humidity (in mass of vapor per unit mass of gas) can be converted to each other.

Furthermore, Eq. (2) can be programmed in a computer, e.g., an electronic digital computer, microprocessor, and the like, for indicating the humidity based on the reference temperature (i.e., dry-transducer temperature) and the wet-transducer temperature. For determining the concentration of a vapor other than water in a gas, the material, e.g., gel or porous polymeric membrane, surrounding the wet-transducer temperature sensor should be selected to be compatible with the liquid and vapor, as well as the gas in which the dual-transducer temperature sensor is to be used. The material should be selected to allow adequate mass transfer of the liquid from the liquid at the liquid-permeable material to the gas.

Figure 6:
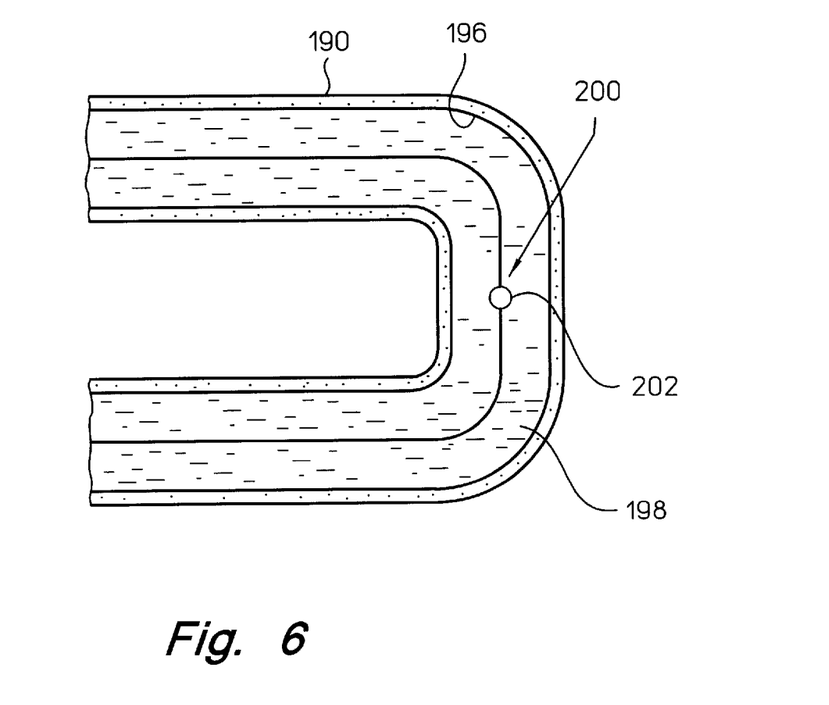
FIG. 6 shows a sectional view in portion of a wet-transducer temperature sensor of yet another dual-transducer temperature sensor in accordance with the present invention

In yet another embodiment, a dual-transducer temperature sensor can be made to include a gel coating 190 on the outside of a porous tubing 196, which encloses the liquid 198 and the wet-transducer temperature sensor 200, which in turn has a thermocouple junction 202, as shown in FIG. 6 in portion. In this way, a more porous tubing can be used with adequate wetting of the gel coating 190 but without dripping.

The vapor concentration sensor of the present invention can be adapted in an embodiment to be used as a conventional humidity sensor for measuring water humidity in atmospheric air, much like the conventional dry and wet bulb humidity sensor, with the exception that instead of a wick, a gel coating or a porous membranous tubing, for example, can be used to provide water to wet the wet-transducer temperature sensor. Other embodiments can be adapted to measure the concentration of, e.g., organic vapors in gas streams. In these cases, the liquid-permeable material, e.g., polymeric components, are selected to be compatible with the gas and vapor and such that the heat and mass transfer are adequate for the humidity sensor (which in these cases measure temperature relating to the non-aqueous vapor concentration) to function properly. For liquids that vaporize faster than water at a particular temperature, e.g., room temperature of about 25° C., a gel coating or a porous membrane that can transfer water faster should be selected so as not to mass-transfer-limit the gel coating or the membrane.

To illustrate the functioning of a humidity sensor of the present invention, the following examples are provided.

EXAMPLE 1

A humidity sensor as shown in FIGS. 3 and 4 was used. In this humidity sensor, the dual-transducer temperature sensor has a support body 174 that is a 3 mm outside diameter (o.d.) multi-lumen tubing. It has three lumens for holding the "dry-transducer" reference thermocouple (or simply "dry thermocouple") 160 and the two legs of the U-shaped porous tubing 170 with the "wet-transducer" thermocouple 164. An example of thermocouples that can be used is Product No. EI1110109/TT-K-40, Omega Engineering Inc. Stamford, Conn. The thermocouple 160 wires 168A, 168B are insulated and encapsulated in a polymeric sheath. The thermocouple junction 166 is made up of bare wires, preferably of chromium-nickel alloy CHROMEL and aluminum-nickel alloy ALUMEL (Omega Engineering Inc.), although other types of thermocouple junctions can also be used. In this example, the thermocouple wires are 0.002 inch (50 μm) in diameter. The wet-transducer thermocouple is inserted in a hydrophilic porous capillary tubing (e.g., CUPROPHAN V0.021 cellulose tubing by Enka Glanzstoff AG, Charlotte, N.C., now a subdivision of AKZO Nobel Frazer AG, 28 Oehder Strasse, 42201, Wuppertal, Germany) of about 2.5 mm length and about 0.007 inch (175 μm) inside diameter (i.d.) and 0.01 inch (250 μm) outer diameter (o.d.). Preferably, a gap of at least 0.001 inch (25 μm) is allowed between the thermocouple junction 166 and the tubing to allow water to flow around and wet the thermocouple junction.

The dry-transducer thermocouple 160 and the wet-transducer thermocouple 164 are placed about 0.5 inch (1.2 cm) apart. The two ends of the U-shaped tubing 170 are connected to the lumen of two of the channels of the support multi-lumen tubing 174 such that water can enter one lumen, pass through the U-shaped tubing 170 and out the other lumen of the support multi-lumen tubing 174. A syringe is connected to the lower lumen to allow injection of water to fill the U-shaped tubing 170 with water. The outer wall of the U-shaped tubing 170 is sealed with epoxy against the lumens of the support multi-lumen tubing 174 to prevent water leakage. A suitable epoxy is LOCTITE 3321 (Loctite Corp., Rocky Hill, Conn.). The two terminals of each of the thermocouples are connected to a thermocouple temperature meter, e.g., Omega Engineering Inc. Microprocessor Thermometer Model HH22, to measure the temperature of the two thermocouple junctions simultaneously.

Figure 7:
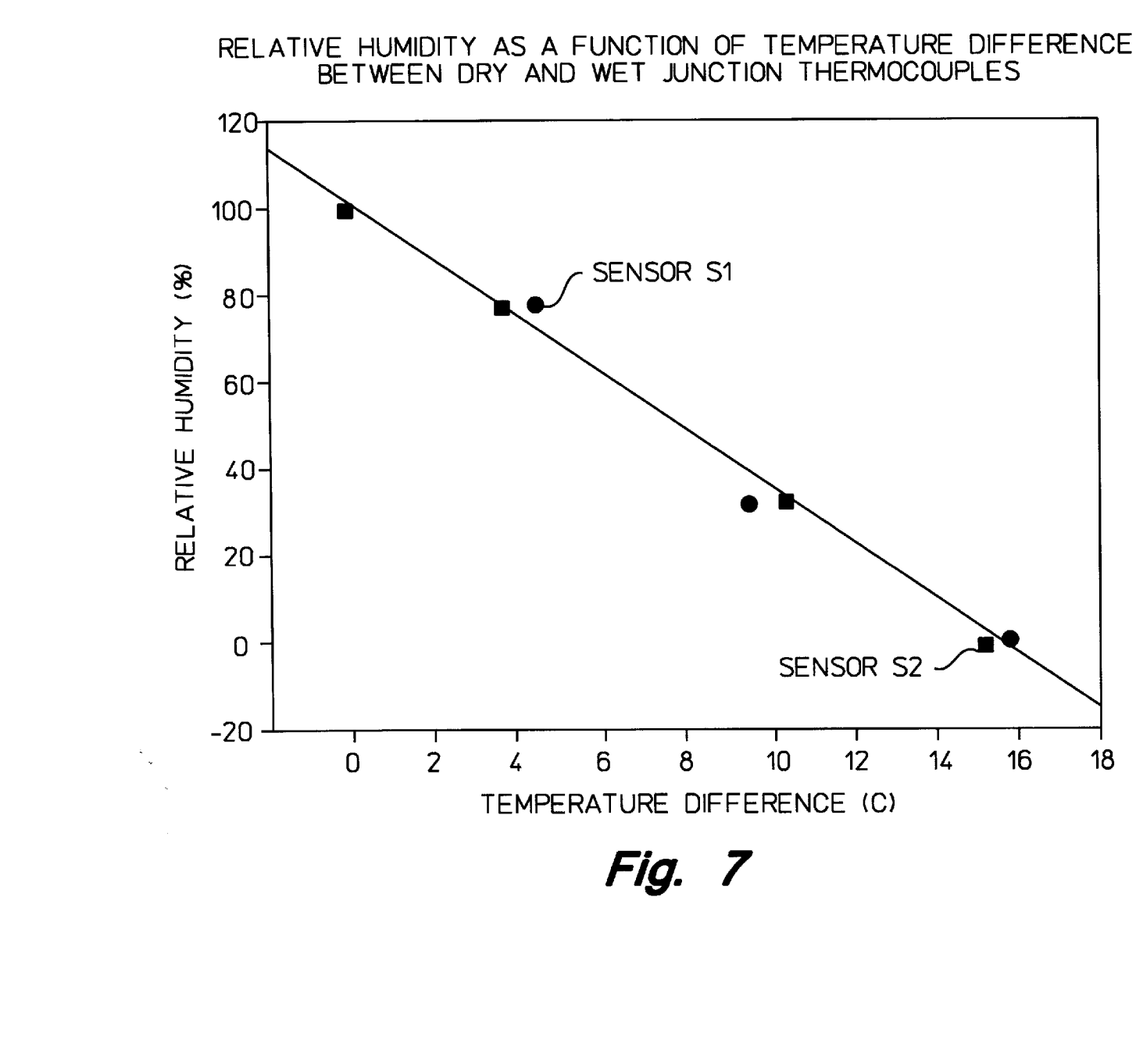
FIG. 7 shows a graph showing the relation between the temperature difference between dry thermocouple and wet-transducer thermocouple and relative humidity applicable in an exemplary run of the present invention.

The difference between the wet-transducer temperature and dry-transducer temperature as related to the relative humidity for the dual-transducer temperature sensor in this example is shown in FIG. 7. The dots present data collected from one humidity sensor S1 and the square represent data collected from an alternative humidity sensor S2 made the same way.

Figure 8:
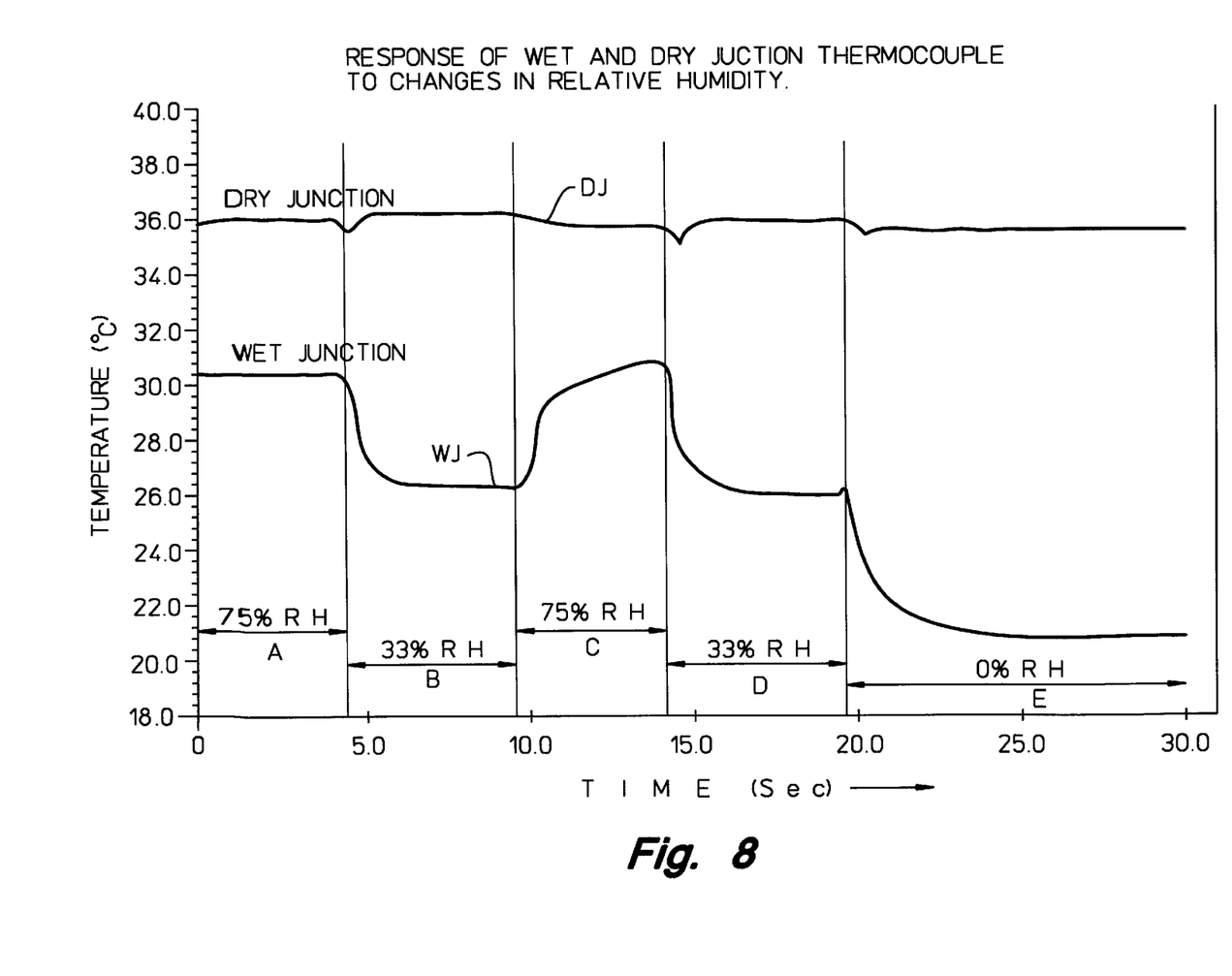
FIG. 8 shows in graphical form the temperature of the dry thermocouple and the wet-transducer thermocouple of a humidity sensor of FIG. 7 in gas streams of different relative humidity.

FIG. 8 shows the response of the dry and the wet-transducer thermocouple junctions associated with the humidity sensor S1 of FIG. 7 when they were inserted in gas streams (i.e., moisture in air) of various relative humidity, the time periods of the administration of the various gas streams are represented in the graph by A (relative humidity, RH, of 75%), B (RH of 33%), C (RH of 75%), D (RH of 33%), and E (RH of 0%). The dry-transducer thermocouple junction, except for artifacts caused by gas stream switching during the brief periods of transition, remains steady in temperature, as shown by curve DJ. Curve WJ shows that the wet-transducer temperature varied inversely with the relative humidity. The response shown is slower than that for the sensor due to the finite time required to switch the vapor sample to provide differences in flow conditions. This humidity sensor responds in less than a second to a change in humidity, which would be adequate for sensing the humidity of a human breath. Based on FIG. 7 and FIG. 8, the relative humidity, and therefore the absolute humidity as well, of an air stream can be determined by using the humidity sensor.

EXAMPLE 2

The humidity sensor S1 of the above Example 1 was adapted for detecting the concentration of ethanol in a gas stream of air containing ethanol. To adapt the humidity sensor for this purpose, the water in the wet-transducer temperature sensor of Example 1 was replaced with ethanol. After calibration and evaluation, it was shown that the sensor operated well for ethanol in a range of about 0 to 5300 Pascals (0 mm Hg to 40 mm Hg) vapor pressure, which corresponds to 0 to 90% saturation at room temperature (about 25° C.). By replacing the ethanol with methanol or isopropanol in the sensor and calibrating appropriately, the sensor will operate to sense concentration of these vapors in gas streams.

Although the preferred embodiment of the present invention has been described and illustrated in detail, it is to be understood that a person skilled in the art, based on the present disclosure, can make modifications within the scope of the invention. For example, the porous membrane can be made with non-polymeric materials or the gel can be replaced with non-polymeric materials, e.g., inorganic materials such as ceramics. Many non-fibrous porous materials are known in the art.

What is claimed is:

1. A sensor for sensing the concentration of a vapor of a liquid in a gas stream, comprising:

a wetable temperature sensor having a heat sensitive part; and a non-woven, non-flaking, liquid-permeable member (LPM) comprising one of a porous membrane, a gel, and a combination thereof, the LPM substantially surrounding the heat sensitive part of the wetable temperature sensor, wherein heat loss due to evaporation of the liquid when the LPM wet with the liquid is placed in the gas stream will result in the temperature sensed by the wetable temperature sensor being lower than the temperature of the gas stream, the lowering in temperature being determinable to determine the concentration of the vapor in the gas stream.

2. The sensor according to claim 1 wherein the LPM is made of a non-fibrous polymeric porous material.

3. The sensor according to claim 1 wherein the LPM is one of the group consisting of a thin water-permeable polymeric membrane and a gel.

4. The sensor according to claim 1 wherein the LPM comprises a polymeric membrane through which water can permeate to be evaporated to determine the humidity corresponding to water vapor in the gas stream.

5. The sensor according to claim 4 wherein the polymeric membrane is a membranous tubing that encloses a body of flowable liquid water that can conduct to be evaporated from the polymeric membrane.

6. The sensor according to claim 4 wherein the polymeric membrane comprises a polymer selected from the group consisting of polyolefin, polysulfone, and cellulose.

7. The sensor according to claim 4 wherein the polymeric membrane is permeable to liquid of a nominal molecular weight (MW) that falls between about 20,000 Daltons and 20 Daltons.

8. The sensor according to claim 4 wherein the polymeric membrane has a upper nominal molecular weight (MW) cutoff that falls between about 1,000 Daltons and 100 Daltons for liquid to pass through.

9. The sensor according to claim 1 wherein the LPM confines an electrical temperature sensor.

10. The sensor according to claim 9 wherein the electrical temperature sensor is selected from the group consisting of a thermistor and thermocouple.

11. The sensor according to claim 1 wherein the LPM includes a gel through which water can permeate to be evaporated to determine the humidity corresponding to water vapor in the gas stream.

12. The sensor according to claim 11 wherein the gel is selected from the group consisting of poly(hydroxyethyl methacrylate), polyacrylamide, poly(vinyl alcohol), and poly(ethylene glycol).

13. The sensor according to claim 1 wherein the LPM is wetted with water from a water container having a water level above the LPM to determine the humidity corresponding to water vapor in the gas stream.

14. The sensor according to claim 1 wherein the heat-sensitive part of the wetable temperature sensor is surrounded by a medium that is continuous from the heat-sensitive part to a body of liquid supply.

15. The sensor according to claim 14 wherein the medium is water and the LPM has a channel containing the water and the wetable temperature sensor has electrical wires extending into the channel to transmit an electrical signal from the wetable temperature sensor corresponding to the temperature sensed thereby.

16. A apparatus for determining the humidity in a gas stream, comprising:

(a) an electrical dry reference temperature sensor for sensing the temperature of the gas stream;

(b) an electrical wet-transducer temperature sensing unit in the vicinity of the dry reference temperature sensor, the electrical wet-transducer temperature sensing unit having a water-permeable polymeric membrane enclosing water and a second temperature sensor electrically connected to measure the temperature of water proximate to the polymeric membrane when placed in the gas stream, the polymeric membrane having a porosity such that the polymeric membrane is not water-transfer limited to allow water to permeate through the polymeric membrane to be evaporated to result in the second temperature sensor sensing a temperature lower than that measured by the dry reference temperature sensor; and (c) computer electrically connected for determining the humidity of the air stream based on the temperature measured by the electrical dry temperature sensor and the temperature measured by the electrical wet-transducer temperature sensing unit;

wherein the electrical dry temperature sensor and electrical wet-transducer temperature sensing unit have heat-sensitive parts that are of a size adequately small to be placed in an airway of a human.

17. The apparatus according to claim 16 wherein the second temperature sensor in the wet-transducer temperature sensing unit is a thermocouple.

18. A method of making a sensor for determining the concentration of a vapor of a liquid in a gas stream:

substantially surrounding a temperature sensor with a non-woven, non-flaking, liquid-permeable member (LPM) comprising one of a porous membrane, a gel, and a combination thereof, the LPM wherein heat loss due to evaporation of the liquid from the LPM when wet with the liquid and in a gas stream will result in a temperature sensed by the temperature sensor being lower than the temperature of the gas stream, the temperature of the temperature sensor when wet and the temperature of the gas stream being determinable to determine the concentration of the vapor in the gas stream.

19. The method according to claim 18 wherein a polymeric membrane through which water permeates to be evaporated is used in the LPM to substantially surround the temperature sensor.

20. The method according to claim 19 wherein the polymeric membrane is used to enclose a body of flowable liquid water that can conduct to be evaporated from the membrane.

21. The method according to claim 18 wherein a polymeric gel through which water can permeate is used in the LPM to substantially surround the temperature sensor.

22. A method for sensing the humidity of a volatile liquid in a gas stream, comprising:

(a) sensing the temperature of the gas stream; and (b) using a thermal sensor to measure the temperature of a medium surrounding the thermal sensor in the gas stream, the medium being continuous from the thermal sensor to a body of supply of the liquid remote from the thermal sensor, the liquid proximate to the thermal sensor being confined by a substantially non-woven, non-flaking, water-permeable member (LPM) comprising one of a porous membrane, a gel, and a combination thereof in the gas stream, wherein heat loss due to evaporation of the liquid from the LPM when wet with the liquid will result in a temperature lower than the temperature of the gas stream, said lowering in temperature being determinable to determine the humidity in the gas stream.

23. A sensor for sensing the concentration of a vapor of a liquid in a gas, comprising:

(a) means for sensing a reference temperature in the gas;

(b) non-woven, non-fibrous, polymeric means comprising one of a porous membrane, a gel, and a combination thereof in the vicinity of the means for sensing a wet-transducer temperature, for allowing the liquid to pass from a liquid supply to vaporize therefrom when the gas is not saturated with the vapor; and (c) means for sensing the wet-transducer temperature of the non-woven, non-fibrous, polymeric means, the difference between the temperature of the means for sensing a reference temperature and the wet-transducer temperature of the non-woven, non-fibrous, polymeric means being determinable to determine the concentration of the vapor in the gas.

24. A sensor for sensing the concentration of a vapor of a liquid in a gas stream, comprising:

a wetable temperature sensor having a heat sensitive part, the heat-sensitive part being surrounded by a liquid medium that is continuous from the heat-sensitive part to a body of liquid supply; and a non-woven, non-flaking, liquid-permeable member (LPM) substantially surrounding the heat sensitive part of the wetable temperature sensor, wherein heat loss due to evaporation of the liquid when the LPM wet with the liquid is placed in the gas stream will result in the temperature sensed by the wetable temperature sensor being lower than the temperature of the gas stream, the lowering in temperature being determinable to determine the concentration of the vapor in the gas stream, the LPM has a channel containing the liquid and the wetable temperature sensor has electrical wires extending into the channel to transmit electrical signal from the wetable temperature sensor corresponding to the temperature sensed thereby.

* * * * *